United States Patent [19]
Ife et al.

[11] Patent Number: 4,935,431
[45] Date of Patent: Jun. 19, 1990

[54] SUBSTITUTED 7-AMINO-THIENOPYRIDINE DERIVATIVES AS GASTRIC ACID SECRETION INHIBITORS

[75] Inventors: Robert J. Ife, Stevenage; Thomas H. Brown, Tewin; Colin A. Leach, Stevenage, all of England

[73] Assignee: SmithKline Beckman Intercredit B.V., Rotterdam, Netherlands

[21] Appl. No.: 314,617

[22] Filed: Feb. 23, 1989

[30] Foreign Application Priority Data

Feb. 25, 1988 [GB] United Kingdom ................. 8804448

[51] Int. Cl.$^5$ ..................... A61K 31/44; C07D 495/04
[52] U.S. Cl. ..................................... 514/301; 546/114
[58] Field of Search ......................... 546/114; 514/301

[56] References Cited

U.S. PATENT DOCUMENTS 2,652,398  9/1953  Kaye .................................... 546/163
3,470,186  9/1969  Hanifin et al. ...................... 546/160

FOREIGN PATENT DOCUMENTS 0126970 12/1984 European Pat. Off. .
0259174  3/1988 European Pat. Off. .
2106612  5/1972 France .
2047244 11/1980 United Kingdom .

OTHER PUBLICATIONS

Chemical Abstracts, 101:22872s; Barker et al.; Thienopyridines, Part 5, p. 548(1984).
Khan et al., J. of Het. Chem., 14, 807–812(1977); Thieno(2,3-b)Pyridines and Thieno(3,2-b)Pyridines.
Chemical Abstracts, 104:5801n, Barker et al., Thienopipedines, Part 6, p. 532(1986).

Primary Examiner—Mary C. Lee
Assistant Examiner—Bernard I. Dentz
Attorney, Agent, or Firm—Dara L. Dinner; Janice E. Williams; Edward T. Lentz

[57] ABSTRACT

Substituted 4-aminothienopyridine derivatives which are inhibitors of gastric acid secretion. A compound of the invention is 6-butyryl-7-(2-isopropylphenylamino)-thieno[3,2-b]pyridine.

11 Claims, No Drawings

SUBSTITUTED 7-AMINO-THIENOPYRIDINE DERIVATIVES AS GASTRIC ACID SECRETION INHIBITORS

The present invention relates to novel substituted quinoline derivatives, processes for their preparation, intermediates useful in their preparation, pharmaceutical compositions containing them and their use in therapy.

Substituted quinoline derivatives having activity as inhibitors of gastric acid secretion are known in the art. In particular, U.S. Pat. No. 4,343,804 and EP No. 259174-A disclose series of 4-phenylaminoquinoline compounds in which the phenyl and quinoline rings are optionally substituted. The present invention relates to novel compounds having activity as inhibitors of gastric acid secretion, which comprise a thienylpyridine nucleus bearing an optionally substituted phenylamino group.

Accordingly, the present invention provides, in a first aspect, a compound of structure (I):

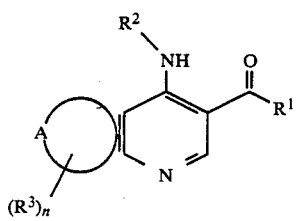

in which $R^1$ is hydrogen, $C_{1-6}$alkyl, $C_{1-6}$alkoxy, $C_{1-6}$alkoxy$C_{1-6}$alkyl, $C_{3-6}$cycloalkyl, $C_{3-6}$cycloalkyl$C_{1-6}$alkyl, phenyl, phenyl$C_{1-6}$alkyl, the phenyl groups being optionally substituted;

$R^2$ is $C_{1-6}$alkyl, $C_{3-6}$cycloalkyl, $C_{3-6}$cycloalkyl-$C_{1-6}$alkyl, phenyl or phenyl$C_{1-6}$alkyl the phenyl groups being optionally substituted by 1–3 radicals selected from $C_{1-6}$alkyl, $C_{1-6}$alkoxy, amino $C_{1-6}$alkylthio, halogen, cyano, hydroxy, carbamoyl, carboxy, $C_{1-6}$alkanoyl or trifluoromethyl;

$R^3$ is hydrogen, $C_{1-6}$alkyl, $C_{1-6}$alkoxy or $COC_{1-6}$alkyl;

n is 1 or 2, and

A is —SCH=CH— or —CH=CHS—;

or a salt thereof.

Suitably, $R^1$ is hydrogen, $C_{1-6}$alkyl, $C_{1-6}$alkoxy, $C_{1-6}$alkoxy$C_{1-6}$alkyl, $C_{3-6}$cycloalkyl, $C_{3-6}$cycloalkyl$C_{1-6}$alkyl, phenyl or phenyl$C_{1-6}$alkyl, the phenyl groups being optionally substituted. Preferably $R^1$ is $C_{1-6}$alkyl, $C_{1-6}$alkoxy, $C_{3-6}$cycloalkyl, or $C_{3-6}$cycloalkyl$C_{1-6}$alkyl. Most preferably $R^1$ is $C_{1-6}$alkyl, in particular ethyl, i-propyl or n-propyl.

Preferably $R^2$ is $C_{1-6}$alkyl, $C_{3-6}$cycloalkyl, $C_{3-6}$cycloalkyl$C_{1-6}$alkyl, phenyl, or phenyl$C_{1-6}$alkyl, the phenyl groups being optionally substituted. More preferably, $R^2$ is a phenyl or phenyl$C_{1-6}$alkyl group the phenyl groups being optionally substituted. Most preferably $R^2$ is a substituted phenyl group in particular a phenyl group substituted in the 2-position by a $C_{1-6}$alkyl or $C_{1-6}$alkoxy group, for example a methyl or methoxy group; or a phenyl group substituted in the 4-position by a halogen, in particular fluorine, and in the 2-position by a $C_{1-6}$alkyl group.

Suitably, n is 1 or 2; preferably n is 1.

Suitably $R^3$ is hydrogen, $C_{1-6}$alkyl, $C_{1-6}$alkoxy, or $COC_{1-6}$alkyl; preferably $R^3$ is hydrogen or $C_{1-6}$alkyl.

$C_{1-6}$alkyl groups (either alone or as part of another group) can be straight or branched.

Phenyl $C_{1-6}$alkyl groups include for example benzyl, phenylethyl, phenylpropyl and phenylbutyl groups, and groups in which the alkyl portion is branched, for example 1-methylbenzyl.

Substituted phenyl and phenyl $C_{1-6}$alkyl groups $R^1$ include, for example phenyl groups substituted by 1 to 3 substituents as hereinbefore described for substituted phenyl groups $R^2$.

It will be appreciated that compounds of structure (I) in which one or more of $R^1$ to $R^3$ is a $C_{3-6}$alkyl group (either alone or as part of another group for example a benzyl or phenethyl group) may contain an asymmetric centre due to the presence of the $C_{3-6}$alkyl group. Such compounds will exist as optical isomers (enantiomers). Both the pure enantiomers, racemic mixtures (50% of each enantiomer) and unequal mixtures of the two are included within the scope of the present invention. Further, all diastereomeric forms possible (pure enantiomers and mixtures thereof) are within the scope of the invention.

Compounds of structure (I) can form pharmaceutically acceptable acid addition salts with suitable organic and inorganic acids the nature of which will be apparent to persons skilled in the art. For example, pharmaceutically acceptable salts can be formed by reaction with hydrochloric, sulphuric, or phosphoric acids; aliphatic, aromatic or heterocyclic sulphonic acids or carboxylic acids such as for example citric, maleic or fumaric acids.

In a further aspect, the present invention provides a process for the preparation of a compound of structure (I) which comprises (a) reaction of a compound of structure (II) with a compound of structure (III):

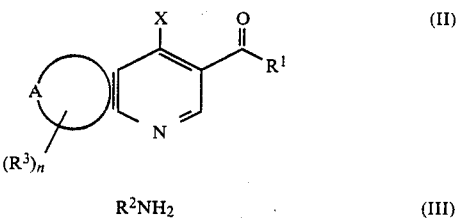

$R^2NH_2$ (III)

in which $R^1$, $R^2$, $R^3$, n and A are as described for structure (I) and X is a group displaceable by an amine;

(b) for compounds of structure (I) in which $R^2$ is $C_{1-6}$alkyl, $C_{3-6}$cycloalkyl, $C_{3-6}$cycloalkyl$C_{1-6}$alkyl or phenyl$C_{1-6}$alkyl reaction of a compound of structure (IV) with a compound of structure (V)

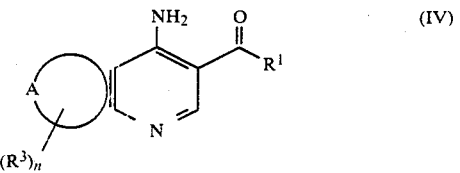

$R^{2'}X^1$ (V)

in which $R^1$, $R^3$, n and A are as described for structure (I); $R^{2'}$ is $C_{1-6}$alkyl, $C_{3-6}$cycloalkyl, $C_{3-6}$cycloalkyl-$C_{1-6}$alkyl or phenyl$C_{1-6}$alkyl and $X^1$ is a leaving group;

(c) reduction of a compound of structure (VI)

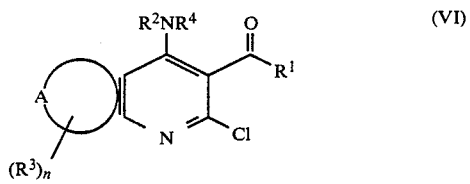

in which $R^1$, $R^2$, $R^3$, n and A are as described for structure (I); and $R^4$ is hydrogen or a nitrogen protecting group;

(d) for compounds of structure (I) in which $R^1$ is other than $C_{1-6}$alkoxy, oxidation of a compound of structure (VII)

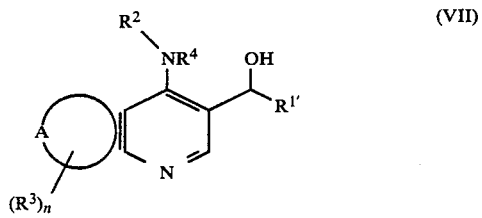

in which $R^2$, $R^3$, n and A are as described for structure (I) $R^1$ is a group $R^1$ other than $C_{1-6}$alkoxy, and $R^4$ is hydrogen or a nitrogen protecting group; and thereafter if desired,
removing any protecting groups;
converting a group $R^1$ into another group $R^1$;
converting a group $R^3$ into another group $R^3$;
forming a salt.

Suitable groups X displaceable by an amine, include for example, halo moieties, aryl or alkylsulphonates, for example, toluene-p-sulphonate or methane sulphonate, alkylthio, alkylsulphonyl, alkylsulphinyl, alkoxy or aryloxy groups. Preferably X is a halo moiety, for example, chloro or bromo, or aryloxy such as phenoxy.

Suitable leaving groups $X^1$ will be apparent to those skilled in the art and include for example a halo moiety, preferably chloro or bromo.

Suitable nitrogen protecting groups $R^4$ will be apparent to those skilled in the art for example as described in "Protective Groups in Organic Synthesis" T. W. Greene, 1981 (Wiley).

The reaction between compounds of structure (II) and compounds of structure (III) is carried out in an organic solvent at a temperature of between ambient and reflux temperature of the solvent used. Suitable solvents include, for example, tetrahydrofuran, dioxan or anisole. Preferably the reaction is carried out at reflux temperature in dioxan as a solvent.

The reaction between compounds of structure (IV) and compounds of structure (V) is carried out in an inert organic solvent at a temperature of between ambient and reflux temperature of the solvent used, preferably in the presence of a strong base. Suitable solvents include for example, dimethylsulphoxide or tetrahydrofuran. Suitable bases include for example, lithium diisopropylamide or dimsyl sodium.

The reduction of a compound of structure (VI) is carried out by for example hydrogenation, over a noble metal catalyst in a suitable solvent. Suitably the reaction is carried out over a palladium on carbon catalyst in ethanol as a solvent.

The compounds of structure (VI) can be prepared from the corresponding compounds of structure (VIII)

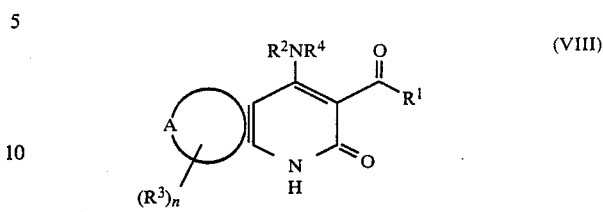

in which $R^1$, $R^2$, $R^3$, $R^4$, n and A are as hereinbefore described, by reaction with, for example, phosphorus oxychloride.

The oxidation of a compound of structure (VII) is carried out in a suitable solvent in the presence of an oxidising agent. Suitable oxidising agents include, for example, manganese dioxide or chromium trioxide.

Suitable interconversions of groups $R^1$ will be apparent to those skilled in the art, for example compounds of structure (I) in which $R^1$ is $C_{2-6}$alkyl, $C_{3-6}$cycloalkyl$C_{2-6}$alkyl or optionally substituted phenyl$C_{2-6}$alkyl can be prepared by alkylation of the following compounds of structure (IA):

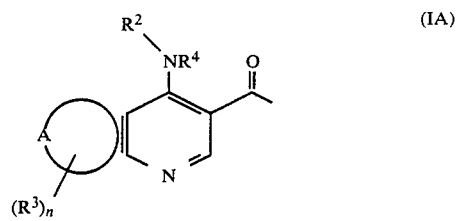

in which $R^2$, $R^3$, n and A are as described for structure (I) and $R^4$ is hydrogen or a protecting group.

The alkylation of compounds of structure (IA) is carried out in the presence of an alkylating agent in a suitable organic solvent at a temperature of between ambient and reflux temperature of the solvent used in the presence of a strong base. Suitable alkylating agents include, for example alkyl or aralkyl halides such as methyl or benzyl iodide and dialkyl sulphates such as dimethyl or diethylsulphate. Suitable strong bases include, for example, sodium hydride, lithium diisopropylamide or dimsyl sodium (the sodium salt of dimethyl sulphoxide). Subsequent removal of any protecting groups present affords the desired compounds of structure (I).

The intermediates of structure (II), (IV), (VI), (VII) and (VIII) can be prepared by standard techniques, or by methods known in the art, for example compounds of structure (II) in which X is Cl, n is 0, $R^1$ is OEt and A is —CH=CHS— or —SCH=CH— can be prepared as described in J. Het. Chem. 14, 807, 1977 and J. Chem. Res. 1726, 1982 respectively. Compounds of structure (II) in which X is Cl, n is 1, $R^3$ is methoxy group in the 3-position of the thiophene ring, $R^1$ is OEt and A is —SCH=CH— can be prepared by the synthetic route outlined in Scheme 1:

SCHEME 1

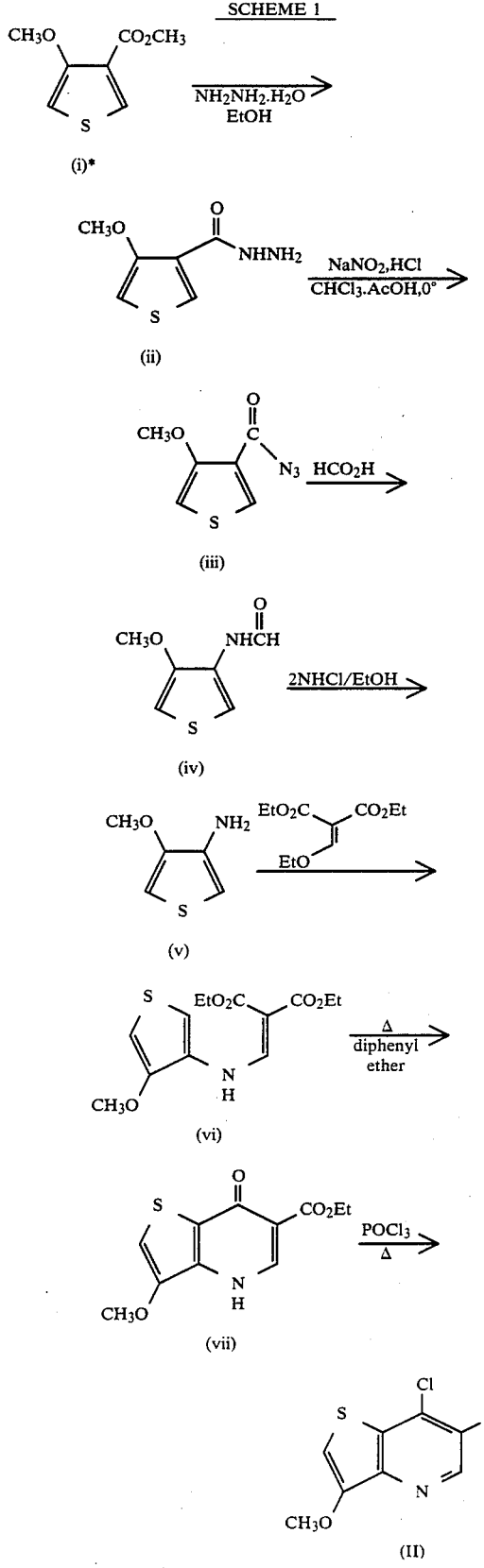

$R^3 = OCH_3$, $n = 1$, $X = Cl$, $A = -SCH=CH-$, and $R^1 = OEt$

*Prepared by the method of J. Org. Chem., 44, 3292, 1979

Similarly, by replacing diethylethoxy methylene malonate with ethyl 2-butyryl-3-ethoxy-prop-2-enoate in the foregoing scheme, compounds of structure (II) in which $R^1$ is an acyl group i.e. a butyryl group can be prepared.

The intermediates of structure (III) and (V) are commercially available or can be prepared by standard techniques.

The compounds of structure (I) and their pharmaceutically acceptable salts exert an anti-secretory effect by inhibition of the gastrointestinal $H^+K^+ATPase$ enzyme (Fellenius, E., Berglindh, T., Sachs, G., Olke, L., Elander, B., Sjostrand, S. E., and Wallmark, B., 1981, Nature, 290, 159–61).

In a further aspect therefore the present invention provides compounds of structure (I) and pharmaceutically acceptable salts thereof for use in therapy. The compounds of structure (I) and their pharmaceutically acceptable salts inhibit exogenously and endogenously stimulated gastric acid secretion and are useful in the treatment of gastrointestinal diseases in mammals, in particular humans. Such diseases include, for example, gastric and duodenal ulcers, aspiration pneumonitis and Zollinger-Ellison Syndrome.

Further, the compounds of structure (I) can be used in the treatment of other disorders where an anti-secretory effect is desirable for example in patients with gastritis, NSAID induced gastritis, acute upper intestinal bleeding, in patients with a history of chronic and excessive alcohol consumption, and in patients with gastro oesophageal reflux disease (GERD).

In therapeutic use, the compounds of the present invention are usually administered in a standard pharmaceutical composition. The present invention therefore provides in a further aspect pharmaceutical compositions comprising a compound of structure (I) or a pharmaceutically acceptable salt thereof and a pharmaceutically acceptable carrier.

The compounds of structure (I) and their pharmaceutically acceptable salts which are active when given orally can be formulated as liquids, for example syrups, suspensions or emulsions, tablets, capsules and lozenges.

A liquid formulation will generally consist of a suspension or solution of the compound or pharmaceutically acceptable salt in a suitable liquid carrier(s) for example, ethanol, glycerine, non-aqueous solvent, for example polyethylene glycol, oils, or water with a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

A typical suppository formulation comprises a compound of formula (I) or a pharmaceutically acceptable salt thereof which is active when administered in this way, with a binding and/or lubricating agent such as polymeric glycols, gelatins or cocoa butter or other low melting vegetable or synthetic waxes or fats.

Preferably the composition is in unit dose form such as a tablet or capsule.

Each dosage unit for oral administration contains preferably from 1 to 250 mg (and for parenteral administration contains preferably from 0.1 to 25 mg) of a compound of the formula (I) or a pharmaceutically acceptable salt thereof calculated as the free base.

The present invention also provides a method of inhibiting gastric acid secretion which comprises administering to a mammal in need thereof an effective amount of a compound of the formula (I) or a pharmaceutically acceptable salt thereof; and a method of treatment of diseases of the stomach or intestine based on increased acid secretion which comprises administering to a mammal in need thereof an effective amount of a compound of the formula (I) or a pharmaceutically acceptable salt thereof.

The pharmaceutically acceptable compounds of the invention will normally be administered to a subject for the treatment of gastro-intestinal diseases and other conditions caused or exacerbated by gastric acidity. The daily dosage regimen for an adult patient may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the formula (I) or a pharmaceutically acceptable salt thereof calculated as the free base, the compound being administered 1 to 4 times per day. Suitably the compounds will be administered for a period of continuous therapy, for example for a week or more.

In addition, the compounds of the present invention can be co-administered with further active ingredients, such as antacids (for example magnesium carbonate or hydroxide and aluminium hydroxide), non-steroidal anti-flammatory drugs (for example indomethacin, aspirin or naproxen), steroids, or nitrite scavengers (for example ascorbic acid or aminosulphonic acid), or other drugs used for treating gastric ulcers (for example pirenzipine, prostanoids for example 16,16 dimethyl $PGE_2$, or histamine $H_2$-antagonists (for example, cimetidine).

The following examples illustrate the invention. Temperatures are recorded in degrees centigrade.

EXAMPLE 1

Ethyl 4-(2-methylohenylamino)thieno[2,3-b]pyridine-5-carboxylate

Ethyl 4-chlorothieno[2,3-b]pyridine-5-carboxylate (4.3 g, 0.0178 mol) and o-toluidine (3.8 g, 0.0356 mol) in anisole (50 ml) were heated under reflux for 24 hours. The reaction mixture was allowed to cool and the solvent evaporated under reduced pressure. The oily residue was taken up in chloroform and extracted with 2N HCl (3×50 ml). The chloroform extracts were washed with sodium carbonate solution, water and dried. Evaporation gave an oil which was purified by column chromatography (silica gel, chloroform eluant) to give a white solid, 2.81 g.

This was crystallised from ethyl acetate to give the title compound, 1.77 g, m.p. 136°–138°.

| | $C_{17}H_{16}N_2O_2S$ | | | |
|---|---|---|---|---|
| Found | C 65.35, | H 5.12, | N 8.94, | S 10.13% |
| Requires | C 65.36, | H 5.16, | N 8.97, | S 10.26% |

EXAMPLE 2

Ethyl 4-benzylaminothieno[2,3-b]pyridine-5-carboxylate

Ethyl 4-chlorothieno[2,3-b]pyridine-5-carboxylate (4.3 g, 0.0178 mol) and benzylamine (3.8 g, 0.0356 mol), were heated in an oil-bath at 140° for 90 minutes. The cooled reaction mixture was dissolved in chloroform, washed with 2N HCl and then aqueous sodium carbonate. The chloroform was washed with water, dried and evaporated to dryness to give an oil which solidified on scratching. This solid was thoroughly triturated with petroleum-ether, b.p. 40°–60°, collected by filtration and dried, 4.3 g. Recrystallisation from ethyl acetate (twice) gave the title compounds as fine, cream crystals 1.29 g, m.p. 84°–86°.

| | $C_{17}H_{16}N_2O_2S$ | | | |
|---|---|---|---|---|
| Found | C 65.40, | H 5.19, | N 8.98, | S 9.98% |
| Requires | C 65.36, | H 5.16, | N 8.97, | S 10.26% |

EXAMPLE 3

Ethyl 7-(2-methylphenylamino)thieno[3,2-b]pyridine-6-carboxylate

Ethyl 7-chlorothieno[3,2-b]pyridine-6-carboxylate (2.1 g, 0.00869 mol) and o-toluidine (1.86 g, 0.0173 mol) in anisole (30 ml) were heated at reflux temperature for 3 hours. After cooling the solvent was evaporated under reduced pressure. The resulting oil was taken up in chloroform and the chloroform washed with 2N NaOH. The aqueous phase was extracted with chloroform (3 times) and the combined chloroform extracts washed with water, dried and evaporated to give an oil. This oil was purified by flash chromatography (silica gel) using dichloromethane as eluant to give a pink solid, 0.76 g.

This was crystallised from ethyl acetate to give the title compound, 0.45 g, m.p. 152°–154°, as off-white crystals.

| | $C_{17}H_{16}N_2O_2S$ | | | |
|---|---|---|---|---|
| Found | C 65.32, | H 5.21, | N 8.91, | S 10.26% |
| Requires | C 65.36, | H 5.16, | N 8.97, | S 10.26% |

EXAMPLE 4

Ethyl 7-benzylaminothieno[3,2-b]pyridine-6-carboxylate

Ethyl 7-chlorothieno[3,2-b]pyridine-6-carboxylate (2.1 g, 0.00869 mol) and benzylamine (1.86 g, 0.0138 mol), were heated in an oil-bath at 160° for one hour. After cooling the solid residue was dissolved in chloroform and washed with 2N.NaOH. The aqueous phase was extracted further with chloroform (twice). The combined chloroform extracts were washed with water, dried and evaporated to give an oil. This oil was purified by flash chromatography (silica gel) using ethyl acetate as eluant to give an off-white solid, 2.2 g.

This was crystallised from diethyl ether to give the title compound, 0.71 g, m.p. 113°–115° as white needles.

| $C_{17}H_{16}N_2O_2S$ | | | | |
|---|---|---|---|---|
| Found | C 65.32, | H 5.02, | N 8.91, | S 10.33% |
| Requires | C 65.36, | H 5.16, | N 8.97, | S 10.26% |

EXAMPLE 5

Ethyl 3-methyl-7-(2-methylphenylamino)thieno[3,2-b]-pyridine-6-carboxylate (a) 4-Methyl-3-aminothiophene-2-carboxylic acid sodium salt (10.4 g, 0.058 mol) and diethylethoxymethylene malonate (12.5 g, 0.058 mol) in toluene (b 100 ml) and glacial acetic acid (3 ml) was heated under reflux for 9 hours. After cooling the solvent was evaporated under reduced pressure and the residue taken up in water, neutralised with sodium carbonate and extracted with chloroform. The chloroform extracts were washed with water, dried and evaporated to give a red oil. This was purified by flash chromatography on silica gel (40–60 mesh) with dichloromethane as eluant to give ethyl 2-ethoxycarbonyl-3-(4-methyl-3-thienylamino)prop-2-enoate, 10.4 g, m.p. 68°–70° (colourless needles from petroleum-ether 40–60).

(b) Ethyl 2-ethoxycarbonyl-3-(4-methyl-3-thienylamino)prop-2-enoate (10.4 g, 0.036 mol) was added to a refluxing solution of freshly distilled diphenylether (110 ml). The reaction mixture was refluxed for 30 minutes, cooled, petroleum ether (b.p. 40°–60°, 100 ml) added and the mixture stirred. The crystalline solid was collected by filtration, washed with petroleum ether (b.p. 40°–60°) and dried to give 3-methyl-6-ethoxycarbonylthieno[3,2-b]pyridin-7(4H)-one, 7.23 g, m.p. 238–242°.

(c) 3-Methyl-6-ethoxycarbonylthieno[3,2-b]pyridin-7(4H)-one (7.0 g, 0.0295 mol) and phosphorus oxychloride (35 ml) were heated under reflux for 2 hours. The excess phosphorus oxychloride was removed by distillation under reduced pressure. The residue was poured onto ice, basified with 2N.NaOH and extracted with chloroform (3×100 ml). The combined chloroform extracts were washed with water, dried and evaporated to dryness to give a buff-coloured solid. This was collected, washed with petroleum ether (b.p. 40°–60°) and dried to give ethyl 3-methyl-7-chlorothieno[3,2-b]pyridine-6-carboxylate, 6.8 g, m.p. 113°–115°.

(d) Ethyl 3-methyl-7-chlorothieno[3,2-b]pyridine-6-carboxylate (3.0 g, 0.0117 mol) and o-toluidine (2.51 g, 0.0234 mol) in anisole (30 ml) were heated under reflux for three hours. The solvent was evaporated under reduced pressure, taken up in chloroform and washed in turn with 2NHCl, $H_2O$, aq$Na_2CO_3$, $H_2O$ and brine, dried and evaporated to give an oil. This oil was purified by flash chromatography (silica, 40–60 mesh) using dichloromethane as eluant to give a buff coloured solid. This was crystallised from methanol to give the title compound, 2.3 g, m.p. 132°–134°.

| $C_{18}H_{18}N_2O_2S$ | | | | |
|---|---|---|---|---|
| Found | C 66.50, | H 5.44, | N 8.56, | S 9.70% |
| Requires | C 66.23, | H 5.56, | N 8.58, | S 9.82% |

EXAMPLE 6

Ethyl 3-methyl-7-benzylaminothieno[3,2-b]pyridine-6-carboxylate

Ethyl 3-methyl-7-chlorothieno[3,2-b)pyridine-6-carboxylate (3.0 g, 0.0117 mol) and benzylamine (2.5 g, 0.0234 mol) were heated in an oil-bath with stirring for 30 minutes (oil-bath temperature to 220°). On cooling the residue was dissolved in chloroform, washed with dilute aqueous sodium hydroxide and the aqueous phase back-extracted with more chloroform. The combined chloroform extracts were washed with water, dried and evaporated to give an oil. This oil was purified by flash chromatography on silica (40–60 mesh) with dichloromethane as eluant to give an oil which crystallised on standing. Recrystallisation from methanol gives the title compound as pale yellow crystals, 3.0 g, m.p. 99°–100°.

| $C_{18}H_{18}N_2O_2S$ | | | | |
|---|---|---|---|---|
| Found | C 66.22, | H 5.37, | N 8.53, | S 9.86% |
| Requires | C 66.23, | H 5.56, | N 8.58, | S 9.82% |

EXAMPLE 7

Ethyl 3-methoxy-7-(2-methylohenylamino)thieno[3,2-b] pyridine-6-carboxylate (a) Methyl 4-methoxy-3-thiophenecarboxylate [1]

Methyl 4-acetoxy-3-thiophenecarboxylate (81 g, 0.40 mol) and concentrated sulphuric acid (5 ml) in methanol (1.25 l) was heated under reflux for 3 days. The solvent was evaporated and the residue diluted with water (300 ml) and extracted with ether (5 times). The ether extracts were combined, washed with 1N sodium hydroxide (3 times) and dried over sodium sulfate. Evaporation of the solvent gave the title compound, 52 g, m.p. 66°–68° (lit. m.p.68°–70°).

[1] J. B. Press, C. M. Hofmann S. R. Safir, J. Org. Chem. 44, 3292, 1979.

(b) 4-Methoxy-3-thiophenecarboxylic acid hydrazide

Methyl 4-methoxy-3-thiophenecarboxylate (50.8 g, 0.295 mol) was refluxed with hydrazine hydrate (30 ml) in methanol (250 ml) overnight. The solvent was evaporated and the residue was diluted with water (300 ml) and extracted with dichloromethane (5×100 ml). The dichloromethane extracts were dried over sodium sulfate, filtered and evaporated under reduced pressure to give the title compound as an off white solid, 49.5 g, m.p. 91°–92°.

(c) 4-Methoxy-3-thiophenecarbonyl azide

4-Methoxy-3-thiophenecarboxylic acid hydrazide (20 g, 0.116 mol) in 3N hydrochloric acid (200 ml), acetic acid (200 ml) and chloroform (300 ml) was cooled to 0°. Sodium nitrite (8 g, 0.116 mol) in water (25 ml) was added dropwise whilst maintaining the temperature at 0°. On completion of the addition the reaction mixture was allowed to warm up to room temperature. The organic layer was separated, washed with sodium bicarbonate solution (3 times), dried over sodium sulphate and the solvent evaporated without heat to give the title compound as a buff-coloured solid, 21.2 g.

(d) N-(4-Methoxy-3-thienyl)formamide

4-Methoxy-3-thiophenecarbonyl azide (21 g, 0.114 mol) was added portionwise to formic acid (97%, 60 ml) heated to boiling. On completion of the addition, the solvent was removed by distillation to give a dark red oil which solidified on cooling. Purification by distillation using a Kugelrohr apparatus gave the title compound, 14 g, b.p. 170° (0.05 mm Hg), m.p. 95°–97°.

(e) 4-Methoxy-3-thiopheneamine

N-(4-Methoxy-3-thienyl)formamide (15 g, 0.095 mol) in ethanolic hydrogen chloride (50 ml) and ethanol (250 ml) was heated under reflux for one hour. The solvent was evaporated under reduced pressure to give a buff coloured solid. The solid was dissolved in water (200 ml) basified with 2N sodium hydroxide solution and extracted with dichloromethane (5×100 ml). The dichloromethane extracts were combined, dried over magnesium sulphate filtered and evaporated to give a dark brown oil, 12.8 g. A sample was purified by distillation on a Kugelrohr apparatus to give the product as a pale yellow oil which solidified on cooling, b.p. 100° (0.02 mm Hg), m.p. 41°–43°.

(f) Ethyl 2-ethoxycarbonyl-3-(4-methoxy-3-thienylamino)prop-2-enoate

4-Methoxy-3-thiopheneamine (11.8 g, 0.091 mol) and diethyl ethoxymethylenemalonate (19.75 g, 0.091 mol) in toluene (300 ml) was heated under reflux in an atmosphere of nitrogen for 18 hours. The solvent was evaporated under reduced pressure to give a buff-coloured solid, this was washed with petroleum ether (b.p. 40°–60°) and the title compound collected by filtration, 25.23 g, m.p. 100°–102°.

(g) 3-Methoxy-6-ethoxycarbonylthieno[3,2-b]pyridin-7-(4H)-one

To a refluxing solution of diphenyl ether (250 ml) was added ethyl 2-ethoxycarbonyl-3-(4-methoxy-3-thienylamino)prop-2-enoate (25 g, 0.0836 mol) portionwise. On completion of the addition, refluxing was continued for a further 20 minutes. The reaction mixture was allowed to cool and then diluted with petroleum ether (b.p. 40°–60°) (400 ml) to give a dark brown solid. This was collected by filtration, washed with petroleum-ether (b.p. 40°–60°) (100 ml) and dried. The solid was recrystallized from DMF (30 ml) to give the title compound as a pale purple solid, 12.7 g, m.p. 244°–247°.

(h) Ethyl 3-methoxy-7-chlorothieno[3,2-b]pyridine-6-carboxylate

3-Methoxy-6-ethoxycarbonylthieno[3,2-b]pyridin-7-(4H)-one (3 g, 0.0118 mol) and phosphorus oxychloride (10 ml) was heated under reflux for one hour. The reaction mixture was poured onto ice (200 g) and stirred for 30 minutes. The mixture was then basified with 40% sodium hydroxide solution and extracted with chloroform (3×100 ml). The chloroform extracts were combined, dried over magnesium sulphate, filtered and evaporated under reduced pressure to give the title compound as a buff-colour solid, 3.2 g, m.p. 135°–137°.

(i) Ethyl 3-methoxy-7-(2-methylphenylamino)thieno-[3,2-b]pyridine-6-carboxylate Ethyl 3-methoxy-7-chlorothieno[3,2-b]pyridin-6-carboxylate (1.5 g, 0.0055 mol) and o-toluidine (1.18 g, 0.011 mol) in anisole (30 ml) were heated under reflux in an inert atmosphere for twenty hours. The solvent was evaporated under reduced pressure and the residue was taken up in chloroform (200 ml) and washed with 2N hydrochloric acid (3×100 ml). The organic phase was then washed with sodium bicarbonate solution (2×100 ml), and water, dried over magnesium sulphate, filtered and evaporated to give an oil. The oil was purified by flash chromatography using dichloromethane as eluant. The fractions containing the product were combined and evaporated to give a colourless product, 1.12 g. Recrystallisation from ethyl acetate gave the title compound, 0.63 g, m.p. 141°–143°.

| | $C_{18}H_{18}N_2O_3S$ | | | |
|---|---|---|---|---|
| Found | C 63.07, | H 5.11, | N 8.18, | S 9.31% |
| Requires | C 63.14, | H 5.30, | N 8.18, | S 9.36% |

EXAMPLE 8

Ethyl 3-methoxy-7-(4-hydroxy-2-methylphenylamino)thieno-[3,2-b]pyridine-6-carboxylate hydrochloride Ethyl 3-methoxy-7-chlorothieno[3,2-b]pyridine-6-carboxylate (1.5 g, 0.0055 mol) and 4-hydroxy-2-methylaniline (1.36 g, 0.011 mol) in anisole (30 ml) were heated under reflux in an inert atmosphere for thirty hours. The solid obtained on cooling was collected by filtration and recrystallised from ethanol to give a brown crystalline solid, 1.09 g. Recrystallisation from ethanol after filtration through charcoal gave the title compound, 0.63 g, m.p. 286°–288°.

| | $C_{18}H_{18}N_2O_4S.0.1H_2O$ | | | |
|---|---|---|---|---|
| Found | C 59.87, | H 5.01, | N 7.72, | S 8.95% |
| Requires | C 60.02, | H 5.09, | N 7.78. | S 8.90% |

EXAMPLE 9

6-Butyryl-7-(2-methylphenylamino)-3-methoxy-thieno[3,2-b]pyridine

(a) Ethyl 2-butyryl-3-(4-methoxy-3-thienylamino)-prop-2-enoate

4-Methoxy-3-thiopheneamine (11 g, 0.085 mol) and ethyl 2-butyryl-3-ethoxyprop-2-enoate (20 g, 0.093 mol)

was heated in an inert atmosphere at 120° for 30 minutes. Addition of petroleum ether, b.p. 40°–60°, 200 ml, gave a solid which was collected by filtration and dried, 17.58 g, m.p. 89°–91°.

(b) 3-Methoxy-6-butyrylthieno[3,2-b]pyridin-7(4H)-one

To a refluxing solution of diphenyl ether (200 ml) was added ethyl 2-butyryl-3-(4-methoxy-3-thienylamino)-prop-2-enoate (16 g, 0.0539 mol) portionwise. On completion of the addition refluxing was continued for a further 20 minutes. The reaction mixture was allowed to cool and then diluted with petroleum ether to give a pale yellow solid, 11.85 g, m.p. 222°–225°.

(c) 6-Butyryl-7-chloro-3-methoxythieno[3,2-b]pyridine

3-Methoxy-6-butyrylthieno[3,2-b]pyridin-7(4H)-one (3 g) and phosphorus oxychloride (10 ml) were heated under reflux for one hour. The reaction mixture was poured onto ice water (100 g) stirred for 30 minutes and then basified with 40% sodium hydroxide solution cooling with ice, then extracted with chloroform (3×100 ml). The chloroform extracts were combined dried over magnesium sulphate, filtered and evaporated under reduced pressure to give a brown solid, 3.1 g, m.p. 76°–78°.

(d) 6-Butyryl-7-(2-methylohenylamino)-3-methoxy-thieno[3,2-b]pyridine

6-Butyryl-7-chloro-3-methoxythieno[3,2-b]pyridine (1.5 g, 0.0056 mol) and 2-methylaniline (1.18 g, 0.011 mol) in anisole (30 ml) were heated under reflux for 20 hours. A further two equivalents of 2-methylaniline were added and the reaction mixture heated under reflux for a further 20 hours. The solvent was evaporated under reduced pressure and the residue taken up in a chloroform and washed with sodium carbonate solution (2×100 ml). The chloroform extract was dried over magnesium sulphate, filtered and evaporated under reduced pressure to give an oil. The product was purified by flash chromatography using dichloromethane as eluant. The product was obtained after chromatography was recrystallised from diethyl ether to give the title compound, 0.36 g, m.p. 128°–130°.

| $C_{19}H_{20}N_2O_2S$ | | | | |
|---|---|---|---|---|
| Found | C 66.83, | H 5.78, | N 8.22, | S 9.41% |
| Requires | C 67.03, | H 5.92, | N 8.23, | S 9.42% |

EXAMPLE 10

6-Butyryl-7-(4-hydroxy-2-methylphenylamino)-3-methoxythieno[3,2-b]pyridine

6-Butyryl-7-chloro-3-methoxythieno[3,2-b]pyridine (1.5 g, 0.0056 mol) and 4-hydroxy-2-methylaniline (1.37 g, 0.011 mol) in anisole (30 ml) were heated under reflux in a nitrogen atmosphere for 36 hours. The solvent was evaporated under reduced pressure and the residue was partitioned between chloroform and sodium bicarbonate solution. The insoluble material was filtered off. The chloroform layer was washed with sodium bicarbonate solution (2×100 ml), dried over magnesium sulphate, filtered and evaporated to give a brown solid. The product was purified by flash chromatography using chloroform as eluant. The solid obtained was recrystallised from ethanol to give the title compound, 0.81 g, m.p. 255°–257°.

| $C_{19}H_{20}N_2O_3S$ | | | | |
|---|---|---|---|---|
| Found | C 64.15, | H 5.64, | N 8.00, | S 9.02% |
| Requires | C 64.02, | H 5.65, | N 7.86, | S 9.00% |

EXAMPLE 11

6-Butyryl-7-(2-methylphenylamino)thieno[3,2-b]pyridine (a) Methyl 3-aminothiophene-2-carboxylate (30 g, 0.18 mol) and a solution of 1M sodium hydroxide (8 g, 200 ml) were heated under reflux for 1 hour. After allowing to cool the reaction mixture was evaporated to dryness. To the solid obtained was added ethyl 2-butyryl-3-ethoxyprop-2-enoate (38.5 g, 0.18 mol), acetic acid (12 g, 0.18 mol) and toluene (500 ml). The reaction mixture was heated under reflux for 20 hours. The solid was filtered off and the filtrate was washed with sodium carbonate solution, dried over magnesium sulphate, filtered and evaporated to give ethyl 2-butyryl-3-thienylaminoprop-2-enoate as a dark red oil, 34.4 g. The oil was used in the next experiment without further purification.

(b) To a refluxing solution of diphenyl ether (185 ml) in a nitrogen atmosphere was added ethyl 2-butyryl-3-thienyl-aminoprop-2-enoate (18.5 g, 0.069 mol). Refluxing was continued for 30 minutes, the solution was cooled, petroleum ether (b.p. 40°–60°, 200 ml) was added and the mixture stirred. The crystalline solid obtained was collected by filtration, washed with petroleum ether (b.p. 40°–60°) and dried to give 6-butyryl-thieno[3,2-b]-pyridin-7(4H)-one, 8.4 g. Recrystallization from methanol gave an analytically pure sample, m.p. 244°–247°.

| $C_{11}H_{11}NO_2S$ | | | | |
|---|---|---|---|---|
| Found | C 59.80, | H 5.00, | N 6.40, | S 14.42% |
| Requires | C 59.71, | H 5.01, | N 6.33, | S 14.49% |

(c) 6-Butyrylthieno[3,2-b]pyridin-7(4H)-one (7.9 g, 0.0357 mol) and phosphorus oxychloride (30 ml) were heated under reflux for 1 hour. After allowing to cool the reaction mixture was poured onto ice basified with concentrated ammonia solution and extracted with dichloromethane (3×150 ml). The combined dichloromethane extracts were dried, filtered and evaporated to dryness to give 6-butyryl-7-chlorothieno[3,2-b]pyridine, 5.5 g. Recrystallization from hexane gave an analytically pure sample, m.p. 78°–80°.

| $C_{11}H_{10}ClNOS$ | | | | | |
|---|---|---|---|---|---|
| Found | C 55.37, | H 4.20, | N 5.86, | S 13.34, | Cl 14.66% |
| Requires | C 55.11, | H 4.20, | N 5.84, | S 13.38, | Cl 14.79% |

(d) 6-Butyryl-7-chlorothieno[3,2-b]pyridine (2.5 g, 0.0104 mol) and o-toluidine (2.23 g, 0,0208 mol) in 1,4-dioxan were heated under reflux for 3 hours. The solvent was evaporated under reduced pressure and the residue obtained was dissolved in dichloromethane (100 ml) and washed with 2NHCl (4×100 ml), then sodium carbonate solution (100 ml). The dichloromethane extracts were dried, filtered and evaporated under reduced pressure to give an oil, which crystallized on the addition of petroleum ether (b.p. 40°–60°). The solid was collected by filtration and dried to give 6-butyryl-7-(2-methylphenylamino)thieno[3,2-b]pyridine, (2.25 g), m.p. 114°–116°. 1 g was recrystallized from hexane to give an analytically pure sample, (0.7 g), m.p. 118°–120°.

|  | $C_{18}H_{18}NOS$ | | | |
|---|---|---|---|---|
| Found | C 69.97, | H 5.76, | N 9.04, | S 10.00% |
| Requires | C 69.65, | H 5.84, | N 9.03, | S 10.33% |

The following compounds were made from 6-butyryl-7-chlorothieno-[3,2-b]pyridine and the appropiate amine using the method 11d.

EXAMPLE 12

6-Butyryl-7-(4-fluoro-2-methylphenylamino)thieno[3,2-b]-pyridine m.p. 153°–155° (ethanol).

|  | $C_{18}H_{17}FN_2OS$ | | | |
|---|---|---|---|---|
| Found | C 65.97, | H 5.21, | N 8.58, | S 9.87% |
| Requires | C 65.83, | H 5.22, | N 8.53, | S 9.76% |

EXAMPLE 13

6-Butyryl-7-(2-ethylphenylamino)thieno[3,2-b]pyridine m.p. 80°–82° (diethyl ether/petroleum ether b.p. 40°–60°).

|  | $C_{19}H_{20}N_2OS$ | | | |
|---|---|---|---|---|
| Found | C 70.22, | H 6.17, | N 8.59, | S 9.96% |
| Requires | C 70.34, | H 6.21, | N 8.63, | S 9.88% |

EXAMPLE 14

6-Butyryl-7-(2-propylphenylamino)thieno[3,2-b]pyridine hydrochloride m.p. 163°–165° (ethanol/diethyl ether).

|  | $C_{20}H_{22}N_2OS \cdot HCl$ | | | | |
|---|---|---|---|---|---|
| Found | C 64.05, | H 6.19, | N 7.25, | S 8.43, | $Cl^-$ 9.20% |
| Requires | C 64.07, | H 6.18, | N 7.47, | S 8.55, | $Cl^-$ 9.46% |

EXAMPLE 15

6-Butyryl-7-(2-isopropylphenylamino)thieno[3,2-b]pyridine m.p. 118°–120° (hexane).

|  | $C_{20}H_{22}N_2OS$ | | | |
|---|---|---|---|---|
| Found | C 70.99, | H 6.76, | N 8.03, | S 9.41% |
| Requires | C 70.97, | H 6.55, | N 8.28, | S 9.47% |

EXAMPLE 16

6-Butyryl-(4-hydroxy-2-methylphenylamino)-thieno[3,2-b]-pyridine m.p. 228°–230° (ethyl acetate).

|  | $C_{18}H_{18}N_2O_2S$ | | | |
|---|---|---|---|---|
| Found | C 66.26, | H 5.57, | N 8.55, | S 10.04% |
| Requires | C 66.23, | H 5.56, | N 8.58, | S 9.82% |

EXAMPLE A

A tablet for oral administration is prepared by combining

|  | Mg/Tablet |
|---|---|
| Compound of structure (I) | 100 |
| lactose | 153 |
| Starch | 33 |
| crospovidone | 12 |
| microcrystalline cellulose | 30 |
| magnesium stearate | 2 |
|  | 330 mg | into a 9 mm tablet.

EXAMPLE B

An injection for parenteral administration was prepared from the following

|  | % w:w |
|---|---|
| Compound of Structure (I) | 0,50% (w:v) |
| 1 M citric acid | 30% (v:v) |
| sodium hydroxide (qs) | to pH 3.2 |
| water for injection EP | to 100 ml |

The compound of Structure (I) is dissolved in citric acid and the pH slowly adjusted to pH 3.2 with the sodium hydroxide solution. The solution is then made up to 100 ml with water, sterilised by filtration and sealed into appropriately sized ampoules and vials.

BIOLOGICAL DATA

A. $H^+K^+$ATPase Activity

The effects of a single high concentration (100 μM) of a compound of structure (I) on $K^+$-stimulated ATPase activity in lyophilised gastric vesicles was determined. Preferred compounds of structure (I) were also tested over a range of concentrations to determine $IC_{50}$ values.

(i) Preparation of Lyonhilised Gastric Vesicles (H/K-ATPase)

Lyophilised gastric vesicles were prepared from pig fundic mucosa after the method of Keeling et. al. (Biochem. Pharmacol., 34, 2967, 1985).

(ii) $K^+$-Stimulated ATPase Activity $K^+$-stimulated ATPase activity was determined at 37° C. in the presence of the following: 10 mM Pipes/-Tris buffer pH 7.0, 2 mM $MgSO_4$, 1 mM KCl, 2 mM $Na_2ATP$ and 3 μg protein/ml lyophilised gastric vesicles. After incubation for 30 minutes, the inorganic phosphate hydrolysed from ATP was determined by the method of Yoda and Hokin (Biochem. Biophys. Res. Commun. 40, 880, 1970).

Compounds of structure (I) were dissolved in dimethylsulphoxide which up to the highest concentration used had no effect on $K^+$-stimulated ATPase activity.

The effect of the highest concentration of each compound of structure (I) on the recovery of a standard amount of inorganic phosphate was also determined.

The results are shown in the following table:

| Example No. | IC$_{50}$ (μM) |
|---|---|
| 1 | 3.0 |
| 2 | 9.71 |
| 3 | 0.62 |
| 4 | 4.3 |
| 5 | 52% @ 10 μM |
| 6 | 51% @ 10 μM |
| 7 | 21 |
| 8 | 37% @ 100 μM |
| 9 | 13 |
| 10 | 39% @ 100 μM |
| 11 | 0.88 |
| 12 | 4.3 |
| 13 | 1.1 |
| 14 | 1.2 |
| 15 | 0.86 |
| 16 | 0.33 |

B. Rat Lumen Perfused Stomach (Pentagastrin Stimulated Gastric Acid Secretion)

Using a modification of the procedure described by Ghosh & Schild (Br. J. Pharmacology, 13, 54, 1958), the compounds of the following examples were found on i.v. administration to cause an inhibition of pentagastrin stimulated gastric acid secretion as indicated in the following table. Results are given as % inhibition at 10 μmole/kg or ED$_{50}$ (μM/kg):

| Compound | RAT GS @ % inhibition 10 μmol/kg) or ED$_{50}$ (μM/kg) |
|---|---|
| 1 | 32% |
| 2 | 13% |
| 3 | 9.7 |
| 4 | 19% |
| 5 | 11.2 |
| 6 | 31% |
| 11 | 55% |
| 12 | 38% |
| 13 | 3.32 |
| 15 | 62% |
| 16 | 4.03 |

What is claimed is:

1. A compound of structure (I):

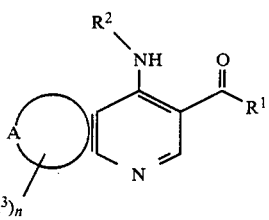

in which

R$^1$ is hydrogen, C$_{1-6}$alkyl, C$_{1-6}$alkoxy, C$_{1-6}$alkoxyC$_{1-6}$-alkyl, C$_{3-6}$cycloalkyl, C$_{3-6}$cycloalkylC$_{1-6}$alkyl, phenyl, phenylC$_{1-6}$alkyl, the phenyl groups being optionally substituted by 1-3 radicals selected from C$_{1-6}$ alkyl, C$_{1-6}$ alkoxy, amino C$_{1-6}$ alkylthio, halogen, cyano, hydroxy, carbamoyl, carboxy, C$_{1-6}$ alkanoyl or trifluoromethyl;

R$^2$ is C$_{1-6}$alkyl, C$_{3-6}$cycloalkyl, C$_{3-6}$cycloalkyl-C$_{1-6}$alkyl, phenyl or phenylC$_{1-6}$alkyl the phenyl groups being optionally substituted by 1-3 radicals selected from C$_{1-6}$alkyl, C$_{1-6}$alkoxy, amino C$_{1-6}$alkylthio, halogen, cyano, hydroxy, carbamoyl, carboxy, C$_{1-6}$alkanoyl or trifluoromethyl;

R$^3$ is hydrogen, C$_{1-6}$alkyl, C$_{1-6}$alkoxy or COC$_{1-6}$alkyl;

n is 1 or 2, and

A is —SCH=CH— or —CH=CHS—;

or a pharmaceutically acceptable salt thereof.

2. A compound according to claim 1 in which R$^2$ is a substituted phenyl group.

3. A compound according to claim 2 in which R$^2$ is a phenyl group substituted by a single substituent in the 2-position of the ring.

4. A compound according to claim 3 in which R$^2$ is a phenyl group substituted by an additional substituent in the 4-position of the ring.

5. A compound according to claim 1 which is 6-butyryl-7-(2-methylphenylamino)thieno[3,2-b]pyridine.

6. A compound according to claim 1 which is 6-butyryl-7-(2-ethylphenylamino)thieno[3,2-b]pyridine.

7. A compound according to claim 1 which is 6-butyryl-7-(2-isopropylphenylamino)thieno[3,2-b]pyridine.

8. A compound according to claim 1 which is 6 butyryl-(4-hydroxy-2-methylphenylamino)thieno[3,2-b]-pyridine.

9. A pharmaceutical composition comprising a compound according to claim 1 or a pharmaceutically acceptable salt thereof and a pharmaceutically acceptable carrier.

10. A method of inhibiting gastric acid secretion which comprises administering to a mammal in need thereof an effective amount of a compound according to claim 1.

11. A method of treatment of gastrointestinal diseases and other conditions caused or exacerbated by gastric acidity which comprises administering to a mammal in need thereof an effective amount of a compound according to claim 1.

* * * * *